US007510872B2

(12) United States Patent
Clark et al.

(10) Patent No.: US 7,510,872 B2
(45) Date of Patent: Mar. 31, 2009

(54) RECOMBINANT ADENO-ASSOCIATED VIRUS PRODUCTION

(75) Inventors: Kelly Reed Clark, Westerville, OH (US); Philip Rudolph Johnson, Jr., New Albany, OH (US)

(73) Assignee: Nationwide Children's Hospital, Columbus, OH (US)

( * ) Notice: Subject to any disclaimer, the term of this patent is extended or adjusted under 35 U.S.C. 154(b) by 0 days.

(21) Appl. No.: 10/789,303

(22) Filed: Feb. 26, 2004

(65) Prior Publication Data

US 2004/0224411 A1 Nov. 11, 2004

Related U.S. Application Data

(60) Provisional application No. 60/450,473, filed on Feb. 26, 2003.

(51) Int. Cl.
*C12N 5/10* (2006.01)
*C12N 7/00* (2006.01)
*C12N 7/02* (2006.01)
(52) U.S. Cl. .................. 435/325; 435/235.1; 435/239
(58) Field of Classification Search .............. 435/457, 435/235.1, 325, 5
See application file for complete search history.

(56) References Cited

U.S. PATENT DOCUMENTS

| 5,622,856 | A | 4/1997 | Natsoulis |
| 5,658,776 | A | 8/1997 | Flotte et al. |
| 5,658,785 | A | 8/1997 | Johnson |
| 5,837,484 | A | 11/1998 | Trempe et al. |
| 5,911,998 | A * | 6/1999 | Potash et al. ............. 424/205.1 |
| 6,027,931 | A * | 2/2000 | Natsoulis et al. ......... 435/235.1 |
| 6,258,595 | B1 | 7/2001 | Gao et al. |
| 6,365,403 | B1 | 4/2002 | Natsoulis et al. |
| 6,429,001 | B1 * | 8/2002 | Hardy ...................... 435/235.1 |
| 6,475,769 | B1 | 11/2002 | Wilson et al. |
| 6,541,258 | B2 | 4/2003 | Allen et al. |
| 6,635,476 | B1 * | 10/2003 | Murphy ................... 435/320.1 |
| 7,235,393 | B2 * | 6/2007 | Gao et al. ................. 435/239 |
| 2004/0224411 | A1 * | 11/2004 | Clark et al. .............. 435/457 |

FOREIGN PATENT DOCUMENTS

WO WO99/41399 8/1999

OTHER PUBLICATIONS

Xiao, X. et al., "Production of High-Titer Recombinant Adeno-Asociated Virus Vectors in the Abscence of Helper Adenovirus", 1998, J. Virol., vol. 72: pp. 2224-2232.*
Collaco, R. et al., "A helper virus-free packaging system for recombinant adeno-associated virus vectors", 1999, Gene, vol. 238: pp. 397-405.*
Aitken et al., *Hum Gene Therapy*, "A Phase I Study of Aerosolized Administration of tgAAVCF to Cystic Fibrosis Subjects with Mild Lung Disease", 12:1907-1916 (2001).
Carter et al., AAV Vectors for Gene Therapy, in Gene and Cell Therapy : Therapeutic Mechanisms and Strategies, Second Edition (Ed. N. Templeton-Smith), pp. 71-101, Marcel Dekker, New York, 2004.
Clark et al., *Hum Gene Therapy*, "Cell Lines for the Production of Recombinant Adeno-Associated Virus", 6:1329-1341 (1995).
Clark et al., *Gene Therapy*, "A stable cell line carrying adenovirus-inducible rep and cap genes allows for infectivity titration of adeno-associated virus vectors", 3:1124-1132 (1996).
Clark et al., *Hum Gene Therapy*, "Recombinant Adeno-Associated Viral Vectors Mediate Long-Term Transgene Expression in Muscle", 8(6):659-669 (1997).
Clark et al., *Hum Gene Therapy*, "Highly Purified Recombinant Adeno-Associated Virus Vectors Are Biologically Active and Free of Detectable Helper and Wild-Type Viruses", 10(6):1031-1039 (1999).
Fan and Dong, *Human Gene Therapy*, "Replication of rep-cap Genes Is Essential for the High-Efficiency Production of Recombinant AAV", 8:87-98 (1997).
Gao et al., *Molecular Therapy*, "Rep/Cap Gene Amplification and High-Yield Production of AAV in an A549 Cell Line Expressing Rep/Cap", 5(5):644-649 (2002).
Graham and Prevec, *Mol. Biotechnol.*, "Methods for Construction of Adenovirus Vectors", 3:207-220 (1995).
Handbook of Parvoviruses, vol. I (P. Tjissen, ed.) CRC Press, Boca Raton, pp. 255-282 (1989).
Leonard and Berns, *Virology*, "Cloning, Expression, and Partial Purification of Rep78: An Adeno-Associated Virus Replication Protein", 200:566-573 (1994).
Li et al., *J. Virol.*, "Role for Highly Regulated *rep* Gene Expression in Adeno-Associated Virus Vector Production", 71:5236-5243 (1997).
Liu et al., *Molecular Therapy*, "Selective Rep-Cap Gene Amplification as a Mechanism For High-Titer Recombinant AAV Production From Stable Cell Lines", 2(4):394-403 (2000).
Matsushita et al., *Gene Therapy*, "Adeno-associated virus vectors can be efficiently produced without helper virus", 5:938-945 (1998).
Muzyczka, *Current Topics in Microbiology and Immunology*, "Use of Adeno-Associated Virus as a General Transduction Vector for Mammalian Cells", 158:97-129 (1992).
Nony et al., *J. Virol.*, "Novel *cis*-Acting Replication Element in the Adeno-Associated Virus Type 2 Genome is Involved in Amplification of Integrated *rep-cap* Sequences", 75(20):9991-9994 (2001).
Pereira et al., *J. Virol.*, "The Adeno-Associated Virus (AAV) Rep Protein Acts as Both a Repressor and an Activator to Regulate AAV Transcription during a Productive Infection", 71(2):1079-1088 (1997).
Ruffling et al., *J. Gen. Virol.*, "Mutations in the carboxy terminus of adeno-associated virus 2 capsid proteins affect viral infectivity: lack of an RGD integrin-binding motif", 75:3385-3392 (1994).
Srivastava et al., *J. Virol.*, "Nucleotide Sequence and Organization of the Adeno-Associated Virus 2 Genome", 45:555-564 (1983).
Vincent et al., *J. Virol.*, "Analysis of Recombinant Adeno-Associated Virus Packaging and Requirements for *rep* and *cap* Gene Products", 71:1897-1905 (1997).

* cited by examiner

*Primary Examiner*—Michael Burkhart
(74) *Attorney, Agent, or Firm*—Marshall, Gerstein & Borun LLP

(57) ABSTRACT

The present invention relates to methods and materials for recombinant adeno-associated virus production. More particularly, the invention relates to use of recombinant adenovirus encoding adeno-associated virus protein in recombinant adeno-associated virus production methods.

31 Claims, 8 Drawing Sheets

Figure 1

```
1                                                                               80
attattgaagcatttatcaggtgtattgtctcatgagcggatacatatttgaatgtatttagaaaataaacaaataggg
gttccgcgcacatttccccgaaaagtgccaacctgacgtctaagaaactattatcatgacattaacctataaaaatag
gcgtatcacgaggccctttcgtcctcgagtttaccactccctatcagtgatagagaaagtgaaagtcgagttaccact
ccctatcagtgatagagaaagtgaaagtcgagttaccactccctatcagtgatagagaaagtgaaagtcgagttac
cactccctatcagtgatagagaaagtgaaagtcgagttaccactccctatcagtgatagagaaagtgaaagtcgagt
taccactccctatcagtgatagagaaagtgaaagtcgagttaccactccctatcagtgatagagaaagtgaaagtc
gagctcgtggtacccgggtcgagtaggcgtgtaccctgacctgtttgacctcgtcgtttagtgaaccgtcagatcg
cctggagacgccatccacgcgttggggtgcgggtcgtggaccctccatagaagacaccgggaccgatccagcctccgcgcccgaattaatt
cccaccatggagctggtcgggtgtcgggtgcctccaactcgcggtcccaaatcaagctgcctggacaatgcggtaccaggaccaggcctc
atacatctccttcaatgcggcctccaactcgcggtcccaaatcaagctgcctggacaatgcgggaaagattatgagcc
tgactaaaaccgccccgactacctgtgggccagcagcccgtggagacatttccagcaatcggattataaatcttg
gaactaaacgggtacgatcccaatatgcggcttccgttcctcgcggaagaccaacatcgcggaggccatagcccacactgtgccctcctacggt
catctggctgttttgggcctgcaactgagaactttccttccacatgtgtcgacaagatggtgatctggtgggaggggaagatg
gcgtaaactgaccaatgagtcggcaaagccattctcggagaagcaaagtgcgcgtgacgtgattgacggaactcaacgaccttcg
accgccaagtcgtggagtcccgtgatcgtcaccaagcggatgttcaaatttgaactcaccgcgtctgatcatgactttgggaaggtcacc
ccagatagaccgactcccgtgcaagaccggatgttcaaatttgaactcaccgcgtctgatcatgactttgggaaggtcacc
aacaccagcagccgttgcaagaccggatgttcaaatttgaactcaccgcgtctgatcatgactttgggaaggtcacc
aagcaggaagtcaaagactttttccggtgggcaaaggatcacgtgttgagtgagcatgaattctacgtcaaaaggg
tggagccaagagagcccgcccccagtgacgacgtagacaggtaccaaaacaaatgttctcgtcacgtgcgcagccat
cgacgtcagagcggaagctgcgatcaatgcgagagaatgaatcagaattcaaatatctgcttcactcacgacagaaagactgtt
atgctgtttccctgcagacaatgcgagagaatgaatcagaattcaaatatctgcttcactcacgacagaaagactgttt
agagtgctttcccgtgtcagaatctcaacccgttctgtcgtcaaaaggcgtatcagaaactgtgctacattcatcata
tcatgggaaagtgccagacgcttgcactgctgcgatctggttatcttccagattggctcgaggacactctctgatctagctagaggat
atgatttaaatcaggtatgctgccgatggttatcttccagattggctcgaggacactctctgatctagctagaggat
ccagacatgataagatacattgatgagtttggacaaccacaactgcagtgaatgcagtgaaaaatgcttattgtgaggat
ttgtgatgctattgctttatttgttaaccattataagctgcaataaacaagttaacaacaac (2061)
```

Annotation - TRE: 184 - 501; Rep 52/40: 647 - 1906

RECOMBINANT ADENO-ASSOCIATED VIRUS PRODUCTION

The present application is based on U.S. Provisional Pat. Application No. 60/450,473, filed Feb. 26, 2003.

FIELD OF THE INVENTION

The present invention relates to methods and materials for recombinant adeno-associated virus production. More particularly, the invention relates to use of recombinant adenovirus encoding adeno-associated virus protein in recombinant adeno-associated virus production methods.

BACKGROUND

Adeno-associated virus (AAV) is a replication-deficient parvovirus, the single-stranded DNA genome of which is about 4.7 kb in length including 145nucleotide inverted terminal repeat (ITRs). The nucleotide sequence of the AAV serotype 2 (AAV2) genome is presented in Srivastava et al., *J. Virol.*, 45: 555-564(1983) as corrected by Ruffing et al., *J. Gen. Virol.*, 75: 3385-3392 (1994). Cis-acting sequences directing viral DNA replication (rep), encapsidation/packaging and host cell chromosome integration are contained within the ITRs. Three AAV promoters, p5, p19, and p40 (named for their relative map locations), drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (Rep 78, Rep 68, Rep 52, and Rep 40) from the rep gene. Rep 78and Rep 68, are respectively expressed from unspliced and spliced transcripts initiating at the p5 promoter, while Rep 52 and Rep 40, are respectively expressed from unspliced and spliced transcripts initiating at the p19 promoter. Rep proteins possess multiple enzymatic properties which are ultimately responsible for replicating the viral genome. Rep 78 and 68 appear to be involved in AAV DNA replication and in regulating AAV promoters, while Rep 52 and 40 appear to be involved in formation of single-stranded AAV DNA. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

When wild type AAV infects a human cell, the viral genome can integrate into chromosome 19 resulting in latent infection of the cell. Production of infectious virus does not occur unless the cell is infected with a helper virus (for example, adenovirus or herpesvirus). In the case of adenovirus, genes E1A, E1B, E2A, E4and VA provide helper functions. Upon infection with a helper virus, the AAV provirus is rescued and amplified, and both AAV and adenovirus are produced.

AAV possesses unique features that make it attractive for delivering DNA to cells in a clinical application, for example, as a gene therapy vector or an immunization vector. AAV infection of cells in culture is noncytopathic, and natural infection of humans and other animals is silent and asymptomatic. Moreover, AAV infects many mammalian cells allowing the possibility of targeting many different tissues in vivo. The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV-vectors less critical. AAV may even be lyophilized. Finally, AAV-infected cells are not resistant to superinfection.

Production of rAAV requires the AAV rep78/68 and rep52/40 genes and expression of their gene products, a DNA of interest flanked by AAV ITRs, helper functions provided by an AAV helper virus, and a cell line comprising these components that is permissive for AAV replication. Examples of helper virus functions are adenovirus genes E1, E2A, E4 and VA (Carter, Adeno-associated virus helper functions. In "Handbook of Parvoviruses"Vol I (P.Tjissen, ed.) CRC Press, Boca Raton, pp 255-282, .1989). Wild type AAV (wt AAV) has one of the largest burst sizes of any virus following infection of cells with AAV and adenovirus. This may be well in excess of 100,000 particles per cell (Aitken et al., *Hum Gene Therapy*, 12:1907-1916, 2001), while some rAAV production systems have been reported to achieve 10e3 or 10e4 particles per cell. Rep proteins are absolutely required for both wt AAV and rAAV replication and assembly of intact infectious particles, as summarized in Carter et al., AAV vectors for gene therapy. In "Gene and Cell Therapy: Therapeutic Mechanisms and Strategies", Second Edition (Ed. N. Templeton-Smith), pp 53-101, Marcel Dekker, New York, 2004) Expression of the rep proteins during the replicative phase of AAV production is both autoregulated and highly coordinated at the transcription level exhibiting both positive and negative regulatory activities. The relative ratio of the rep proteins necessary to achieve rAAV vector production levels equivalent to WT AAV has not been fully understood. See Li et al., *J Virol.*, 71:5236-5243 (1997); Xiao et al., *J Virol*, 72:2224-2232 (1998); Matushita et al., *Gene Therapy*, 5:938-945 (1998); and Carter et al., AAV vectors for gene therapy, in "Gene and Cell Therapy: Therapeutic Mechanisms and Strategies", Second Edition (Ed. N. Templeton-Smith), pp 53-101, Marcel Dekker, New York. Numerous vector production methods have been described which have altered the relative ratios of rep 52/40 and rep 78/68 by decoupling regulation of their respective promoters. See, e.g., Natsoulis, U.S. Pat. No. 5,622,856; Natsoulis et al., U.S. Pat. No. 6,365,403; Allen et al., U.S. Pat. No. 6,541,258; Trempe et al., U.S. Pat. No. 5,837,484; Flotte et al., U.S. Pat. No. 5,658,776; Wilson et al. U.S. Pat. No. 6,475,769; Fan and Dong, *Human Gene Therapy*, 8:87-98 (1997); and Vincent et al., *J Virol*, 71:1897-1905 (1997). This decoupling of the large and small rep proteins at the transcriptional has been-achieved by a number of methods including, replacing the native p5, p19, and p40 native AAV promoters either completely or in some combination with heterologous promoters, inducible promoters; or by physical means of either placing the components on separate genetic elements including without limitation separate plasmids; or by utilizing separate genetic construct for transducing or transfecting the permissive cell line including carrier viruses such as adenovirus or herpes virus; inserting additional spacer elements, or physically rearranging the rep gene or its regulatory sequences within a single genetic construct. These strategies have been employed both for transient production systems where one or more of the components are introduced to the permissive cell line via plasmid transfection; hybrid viral infection such as recombinant adenoviruses, herpes virus, or baculovirus; or in stable cell line approaches utilizing production from transformed cancerous cells permissive for AAV production such as HELA and 293 cells.

A requirement for the clinical use of recombinant AAV for DNA delivery is a highly efficient scheme for production of infectious recombinant virus that is reproducible and commercially scalable. In addition, in certain applications such as rAAV use as vectors for inducing immunity it may be desirable to produce rAAV in cells that are noted based upon transformed cancer cell lines or that have demonstrated pharmacovigilance profiles. There thus remains a need in the art for alternative production methods and materials.

SUMMARY OF THE INVENTION

The present invention provides methods and materials useful for producing infectious recombinant AAV (rAAV). Compared to previous methods and materials, the methods and materials of the invention allow more rAAV genomes of lengths approaching wild type AAV genome length (about 4.7 kb) to be encapsidated into infectious rAAV particles and/or allow production of rAAV in cells other than transformed cancer cells.

In one embodiment, methods and materials are provided for increased AAV Rep 52 and Rep 40 protein expression in cells producing rAAV. In contrast to previous methods which rely on decreasing the expression of Rep 78 and 68proteins, the present inventors contemplate that rAAV can be better produced not by intentionally decreasing expression of Rep 78 and 68 protein but instead by intentionally overexpressing Rep 52 and Rep 40 proteins and/or providing supplemental Rep 52 and Rep 40 proteins. The inventors contemplate that Rep 78and Rep 68 proteins in their cells and methods are expressed at about the same level as if the proteins were being expressed in the same system from a construct comprising the p5 promoter and rep DNA in their native conformations. For example, in methods and cells of the invention exemplified below, Rep 78 and Rep 68 proteins are expressed from the AAV p5 promoter in native conformation. Thus it is contemplated with respect to this embodiment of the invention, that methods and cells of the invention overexpress Rep 52 and Rep 40 proteins, but no attempt is made to intentionally decrease expression of Rep 78 and Rep 68 proteins (e.g., no attempt is made to genetically down-regulate Rep 78 and Rep 68 protein expression).

The invention thus provides an infectious recombinant adeno-associated virus-producing cell that contains a rAAV genome, AAV rep-cap proteins and AAV helper functions and that overexpresses AAV Rep 52 and Rep 40 proteins while expressing AAV Rep 78 and Rep 68 proteins at about the level as if controlled by the p5 promoter in native conformation.

Numerous appropriate rAAV genomes are described in the art and may be used in the invention. rAAV genomes usually comprise one or more DNAs of interest flanked by AAV ITRs or an expression cassette (one or more DNAs of interest operatively linked to a promoter and polyadenylation signal for expression) flanked by AAV ITRs. The DNAs of interest may encode a protein or a catalytic, RNA, as is understood in the art.

The rAAV-producing cell produces all AAV rep and cap proteins but, in addition, overexpresses Rep 52 and 40 proteins or contains supplemental Rep 52 and 40 proteins.

AAV helper functions are those helper functions provided by a helper virus of AAV. Helper viruses of AAV are known in the art and include, for example, adenovirus and herpesvirus. Helper virus may be used to infect the cell or helper virus protein alone may be expressed in, or provided to, the cell.

As discussed above, the cell has not been manipulated to produce Rep 78 and Rep 68 proteins at intentionally decreased levels compared to levels that would be normally expressed from the wild-type p5 promoter in that same or equivalent cell.

It is contemplated that any comparison of expression levels of rep proteins may be conducted at the RNA and/or protein level and may be analyzed by techniques standard in the art such as Northern blotting or Western blotting.

Methods of producing such a cell are provided by the invention. One method involves providing AAV helper functions to a cell containing a rAAV genome and AAV rep-cap proteins, then subsequently infecting the cell with any appropriate recombinant vector encoding AAV Rep 52 and Rep 40 proteins and culturing the resulting rAAV-producing cell. The recombinant vector may comprise a viral vector such as a recombinant adenovirus vector. The recombinant adenovirus vector may be made or derived from a human or simian adenovirus vector.

The invention provides rAd that stably express the AAV Rep52 and Rep 40proteins. A rAd of the invention is the replication competent E3-deleted rAd type 5viral vector rAd5/E3/TRE-rep52/40-3.1. Expression of the Rep 52 and Rep 40 proteins in rAd of the invention may be driven by a Ad promoter or by another promoter. The promoter may be an inducible promoter. rAd of the invention may be an E1-deleted, rather than E3-deleted rAd, if E1 is provided to, or found in, the cells that are to produce rAAV.

In the method, the cells may be stably transformed with the rAAV genome and AAV rep-cap genes. Such transformed cells are described in U.S. Pat. No. 5,658,785; Clark et al., *Hum. Gene. Ther.*, 10(6): 1031-1039 (1999); and Clark et al., *Hum. Gene. Ther.*, 8(6): 659-669 (1997), each of which are incorporated by reference herein.

As stated above, in this method the transformed cells are first provided with AAV helper functions and then subsequently infected with a rAd of the invention. A preferred time for infection of cells with rAd of the invention is between about 12and about 18 hours after after provision of AAV helper functions.

In another method for generating such cells, supplemental AAV Rep 52 and Rep 40 proteins are introduced into a cell containing a rAAV genome and AAV rep-cap proteins, AAV helper functions are provided to the cell and the resulting rAAV-producing cell is cultured. The supplemental AAV Rep 52 and Rep 40 proteins may be introduced by introducing an additional AAV rep52/40 expression cassette into the cell.

The rAAV-producing cells of the invention may be HeLa cells, 293 cells and PerC.6 cells (a cognate 293 line). The rAAV-producing cells of the invention may also be cells that are not transformed cancer cells such as low passage 293 cells (human fetal kidney cells transformed with E1 of adenovirus), Vero cells (monkey kidney cells) and FRhL-2 cells (rhesus fetal lung cells). If the cells are human cells the rAd used in the methods is derived from a human Ad. If the cells are simian cells (e.g., Vero or FRhL-2 cells) the rAd used in the methods is derived from a simian Ad.

In another embodiment, the rAAV-producing are simian cells. Such cells may be made by any of the methods described herein wherein a simian Ad helper virus functions are used. One method specific method contemplated is infecting simian cells stably transformed with a rAAV genome and rAAV rep-cap DNA according to U.S. Pat. No. 5,658,785; Clark et al., *Hum. Gene. Ther.*, 10(6):1031-1039(1999); and Clark et al., *Hum. Gene. Ther.*, 8(6): 659-669 (1997)(all of which are incorporated by reference above) with a simian Ad such as SV-20 (ATCC VR-199), and culturing the resulting rAAV-producing cell. In such methods, use of the simian Ad helper virus functions increases the expression of AAV rep proteins in comparison to the expression of AAV rep proteins observed when a human Ad helper virus is used. The simian Ad helper virus used may be optimally matched to the serotype of the rAAV ITRs as would be understood by a person skilled in the art. Additional simian helper viruses useful in methods of the invention may be identified by screening rAAV ITR serotypes, pseudotypes oe chimeras in combination with simian viruses known in the art in a simian cell of interest for the ability to support production of infectious rAAV.

In yet another embodiment of the invention [particularly useful for, but not limited to, rAAV-producing cells such as MRC-5 cells (human fetal fibroblasts) and WI-38 cells (human fetal fibroblasts) that are not transformed cancer cells and are cells that undergo senescence after a limited number of population doublings] may be made by a method of the invention. In the method, a cell is infected with one or more rAd and one or more recombinant vaccinia viruses (rVV) containing DNA in expression cassettes and the resulting rAAV-producing cell is cultured. The rAd(s) provide a rAAV genome and AAV cap DNA, the rVV provides rAAV rep 78 DNA and either rAd or rVV provides rAAV rep52/40 DNA.

In one method, cells that are to produce rAAV are infected with E3-deleted rAd encoding Rep52/40 proteins, E3-deleted rAd encoding AAV cap proteins and E3-deleted rAd containing a rAAV genome, and the cells are also infected with vaccinia virus encoding AAV Rep78/68 proteins. Leonard and Berns, *Virology*, 200: 566-573 (1994) describes methods that can be used to generate such vaccinia virus and is incorporated by reference herein. Alternatively, the cells are infected with E3-deleted rAd-both encoding AAV cap proteins and containing an rAAV genome, and are infected with vaccinia virus encoding both the AAV Rep78/68 and Rep52/40 proteins. Again, rAd of the invention may be E1-deleted, rather than E3-deleted, rAd if E1 is provided to, or found in, the cells that are to produce rAAV.

It is contemplated that AAV and Ad DNA, or viruses, used in the invention may be derived from any AAV serotype, or any human or non-human primate Ad serotype, for which recombinant viruses can be derived as would be understood by a person skilled in the art.

Infectious rAAV are produced by culturing rAAV-producing cells generated by methods of the invention and isolating the rAAV by methods standard in the art. Infectious rAAV generated by the cells described herein which are either non-cancerous and/or have been previously used for the production of FDA-accepted biologics are particularly useful for eliciting an immune response in a human and vaccine production.

Numerous other aspects and advantages of the present invention will be apparent upon consideration of the following drawing and detailed description.

BRIEF DESCRIPTION OF THE DRAWING

FIG. 1 is the DNA sequence (SEQ ID NO: 1) of a 2,061 bp restriction fragment from plasmid pTRE-Rep52/40 comprising the TRE-Rep52/40 expression cassette.

DETAILED DESCRIPTION

Figure 2:
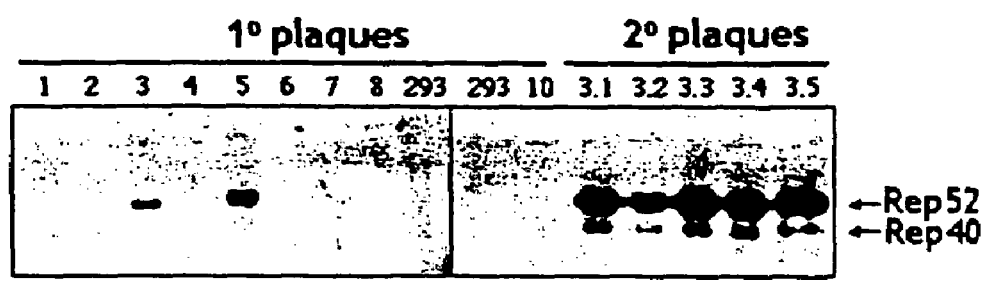
FIG. 2 shows Rep western blot analysis of primary and secondary plaque isolates following infection of 293 cells to generate rAd5/E3/TRE-rep52/40.

The present invention is illustrated by the following examples relating to the production of rAAV using a recombinant, E3-deleted Ad type 5 viral vector (designated rAd5/E3/TRE-rep52/40-3.1) that stably expresses AAV-2 Rep52 and Rep40 proteins. Example 1 describes the construction of plasmid pTRE-Rep52/40. Example 2 describes the molecular cloning of the TRE-Rep52/40 expression cassette into a rAd type 5 shuttle plasmid. Example 3 describes the generation of rAd5/E3/TRE-rep52/40-3.1. Example 4 describes the use of rAd5/E3/TRE-rep52/40-3.1to produce rAAV in HeLa cells. Example 5 describes stable rAAV producer cells lines containing an additional rep52/40 gene expression cassette. Also illustrating the invention are the following examples relating to other embodiments of the invention involving production of rAAV in non-cancerous cells. Production of rAAV in Vero and MRC-5 cells is described in Example 6. Finally, Example 7 describes purification methods for rAAV produced by methods of the invention.

EXAMPLE 1

Molecular Cloning of Plasmid pTRE-Rep52/40

The AAV-2 Rep52/40 open reading frame (1,260 base pairs) was PCR amplified using plasmid pBS/rep-cap/neotk [Clark et al., *Hum. Gene Ther.*, 6:1329-1341 (1995)] as the DNA template. The AAV-2 rep 52/40 sequences were amplified by PCR using the following primers: forward primer 5'CCGTGAATTCCC ACCATGGAGCTGGTCGGGTG-GCTCG 3' (SEQ ID NO: 2) and reverse primer 5'CCGT-GTCTAGA TCAGAGAGAGTGTCCTCGAGC 3' (SEQ ID NO: 3). A 100 ul PCR reaction was performed using Pfu Turbo Polymerase (Stratagene) under standard PCR cycling conditions (1 cycle at 95° C. for 5 minutes; 30 cycles at 95° C. for 1 minute, at 55° C. for 30 seconds, and at 72° C. for 2 minutes, 30 seconds; and 1 cycle at 72° C. for7 minutes). The resulting 1.26 kb PCR product was gel isolated and purified using the Qiagen PCR Clean-up Kit and subsequently digested with restriction enzymes EcoR I and Xba I. The restriction digested 1.26 kb rep52/40 PCR fragment was cloned into the 3.1 kb pTRE commercial vector (Clontech) that was also digested with EcoR 1 and Xba I restriction enzymes using the Rapid DNA Ligation Kit (Roche). The resulting ligation mixture was used to transform MAX Efficiency DH5α competent cells (Gibco BRL) and plated onto LB/Ampicillin medium. Recombinant colonies were screened and identified by restriction enzyme digestion (EcoR I and Xba I), yielding 3 pTRE-Rep52/40 plasmid clones (clone numbers 2, 3, and 4). Clone 2 was chosen for further work.

EXAMPLE 2

Molecular Cloning of the TRE-Rep52/40 Expression Cassette into the Recombinant Adenovirus type 5 Shuttle Plasmid The TRE-Rep52/40 expression cassette was released from clone 2 as a 2,061 bp DNA restriction fragment from plasmid pTRE-Rep52/40 by digestion with Ssp I and Mfe I flanking restriction enzymes and gel band isolated. The DNA sequence of the restriction fragment (SEQ ID NO: 1) is set out in FIG. 1. The TRE-Rep52/40fragment was blunt-ended using T4 DNA polymerase prior to cloning into the Sca I site of the adenovirus shuttle vector pAb26 (Microbix, Inc.) using the Rapid DNA Ligation Kit (Roche). The resulting ligation mixture was used to transform MAX Efficiency DH5α competent cells (Gibco BRL) and plated onto LB/ampicillin medium. Recombinant colonies were screened and identified by restriction enzyme digestion and two recombinant clones were identified (clones 30and 35) that yielded plasmid pAb26/TRE-Rep52/40 (15.97 kb in size). A single clone (#30) was analyzed for Rep52/40 expression by transient plasmid transfection of 293 cells to confirm the structural integrity of the Rep52/40 coding sequences. Western blot analysis using the commercial anti-AAV Rep antibodies (Clones 303.9 and 226.7, American Research Products) confirmed the expected Rep52/40expression.

EXAMPLE 3

Generation of an E3-deleted, Replication Competent Recombinant Adenovirus type 5 Expressing the AAV-2 Rep52 ad Rep40 Proteins The method of Graham and Prevec, *Mol. Biotechnol.*, 3: 207 (1995) was used to generate a recombinant adenovirus type 5 expressing AAV-2 Rep52/40proteins. The method is based on in vivo homologous recombination in 293 cells between shared adenovirus sequences present on the pAB26 shuttle plasmid and a larger helper adenovirus plasmid (pFG173, Microbix, Inc.) that contains the majority of the adenovirus genome. Introduction of this plasmid pair (pAB26 and pFG173) into 293 cells by DNA transfection allows for the generation of recombinant type 5 adenoviruses that contain an insertion in the E3 early region. Since this region is dispensable for adenovirus growth in culture, the resulting recombinant virus is replication competent. Accordingly, low-passage 293 cells (106 cells per dish, 6 dishes total) were transfected with DNA plasmids pFG173 (10ug per dish) and pAB26/TRE-rep52/40 (clone 30, 10 ug per dish) using the CaPO4precipitation method of DNA transfection. Twenty-one days post-transfection, adenovirus induced cytopathic effect became visible in two of the transfected cell dishes. Clarified cellular lysates from each plate were generated by 3 freeze/thaw cycles and shown to possess Rep52/40 activity based on western blot analysis.

The clarified cell lysates were serially diluted (10-fold) and used to infect 293 cells that were subsequently overlaid with nutrient agarose to isolate primary plaque viral isolates. Forty-eight hours post-infection, cell lysates were analyzed by Western blot using a 1:1 cocktail of commercial anti-AAV Rep antibodies (Monoclonal antibodies 303.9 and 226.7, American Research Products) at a dilution of 1:50. Rep protein was visualized using an anti-mouse-HRP conjugated secondary antibody (1:5000 dilution, Sigma), followed by visualization using the ECL Western Blot Detection Kit (Amersham). Results are shown in FIG. 2 wherein control samples containing uninfected 293 cell lysate are labeled "293". Two primary plaque isolates (3 and 5) were identified that expressed Rep52 and to a lesser extent Rep40 and were termed rAd5/E3/TRE-rep52/40-3 and rAd5/E3/TRE-rep52/40-5, respectively.

Rep52/40 expression was originally intended to be controlled by the tetracycline induction system (hence, inclusion of the TRE upstream of the rep52/40gene). However, Rep52/40 expression occurred in the absence of the tTA regulatory protein (FIG. 1). Because the Rep52/40 reading frame was oriented 5'to 3' relative to the upstream major late promoter element (MLP), it is likely that transcriptional read-through into the E3 region from the MLP element explained the tTA independent expression.

A second round of plaque purification was performed on isolate 3 and all secondary viral isolates analyzed expressed Rep52 and Rep40 (FIG. 2, isolates 3.1, 3.2, 3.3, 3.4, 3.5). Secondary plaque isolate 3.1 was expanded in 293 cells and a large-scale viral preparation generated (2×107 pfu/ml).

Figure 3:
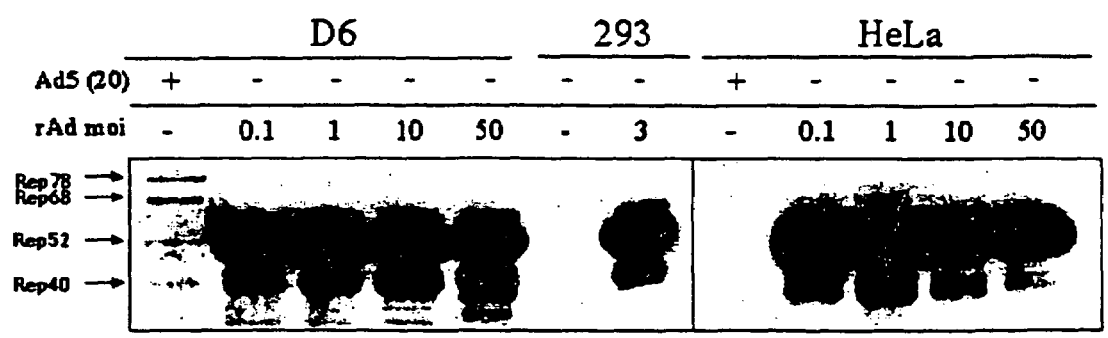
FIG. 3 shows western blot analysis for rep expression of cell lysates following infection with rAd5/E3/TRE-rep52/40.

To confirm stable expression of Rep52 and Rep40 proteins by the rAd5, three cell lines were infected with the virus stock (rAd5/E3/TRE-rep52/40-3.1) at multiplicities of infection (moi) ranging from 0.1 pfu per cell to 50 pfu per cell. As shown in FIG. 3, three cell lines were analyzed (HeLa, 293, and D6). D6cells are a HeLa derived cell line that expresses all four AAV-2 Rep proteins following Ad5 infection and served as the positive control to delineate the position of all 4 Rep proteins (lane 1). Robust expression of Rep52 and Rep40 was observed at all multiplicities of infection assayed (0.1, 1, 3, 10, or 50). All three cell types (HeLa, 293, and D6) infected demonstrated robust Rep52 and Rep40 expression. This stable expression is in contrast to rAd encoding Rep 78 and 68 which lose their Rep78/68 insert over time.

EXAMPLE 4 rAAV-2 Vector Production in HeLa Cells rAAV was produced by rAd5/E3/TRE-rep52/40-3.1 infection of the rAAV-2/β-gal producer cell line D6 [a HeLa cell producer line that yields rAAV2/β-gal that is described in Clark et al., *Hum. Gene. Ther.*, 10(6): 1031-1039 (1999); and Clark et al., *Hum. Gene. Ther.*, 8(6): 659-669 (1997)].

In initial experiments, infection of D6 cells with rAd5/E3/TRE-rep52/40-3.1alone yielded little or no rAAV-2/β-gal., Analysis of Rep expression levels indicated that rapid overexpression of the Rep52 and Rep40 proteins (mediated by rAd5/E3/TRE-rep52/40-3.1) inhibited Rep78 and Rep 68 expression (which are absolutely required for rAAV-2 vector synthesis).

Figure 4:
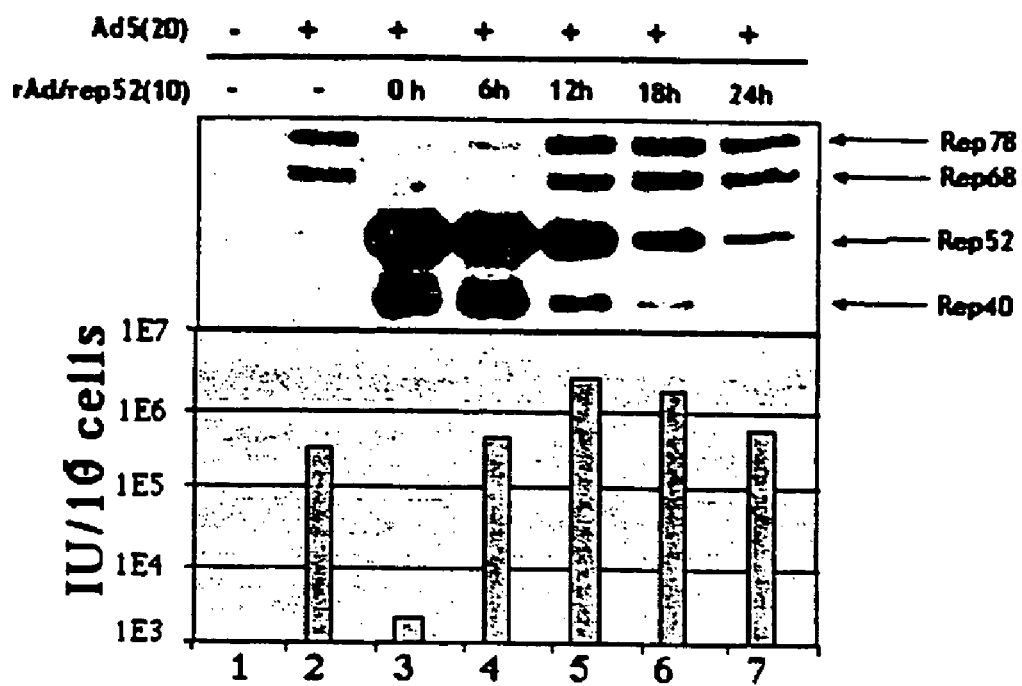
FIG. 4 shows a temporal effect of Ad5/E3/TRE-rep52/40-3-3.1 infection.

To overcome this inhibition, initial and early expression of Rep78 and Rep 68 was obtained by infecting D6 cells with wild-type Ad5 before infecting with rAd5/E3/TRE-rep52/40-3.1. A time course of Ad5 and rAd5/E3/TRE-rep52/40-3.1co-infection was performed, whereby D6 producer cells were initially Ad5infected, then at progressively later time points, the cells were also infected with rAd5/E3/TRE-rep52/40-3.1. After development of maximum adenovirus cytopathic effect, cells were analyzed for Rep expression and infectious rAAV-2/β-gal yields. Results are presented in FIG. 4 wherein the top panel is Rep western blot analysis of D6 cell lysates following infection with wild-type Ad5 alone (moi 20, lane 2)or co-infection with rAd5/E3TRE-rep52/40-3.1 (moi=10, lanes 3-7). Time (h) denotes how many hours following wild type Ad5 infection the rAd vector was added to the D6 cells. The bottom panel of FIG. 4 depicts the yield of infectious rAAV-2/β-gal from D6 cells under the indicated infection conditions. Infectious rAAV-2/β-gal titers were determined as previously described in Clark et al., *Gene Ther.*, 3:1124-1132 (1996).

Co-infection with both viruses yielded very little rAAV-2 vector (FIG. 4, lane 3). However, at 12 and 18 hours post-Ad5 infection, infection with rAd5/E3/TRE-rep52/40-3.1 resulted in efficient overexpression of Rep52 and Rep40, in the presence of Rep78 and Rep68 expression. These infection conditions (12 and 18 hours post-infection) resulted in an increase in infectious rAAV-2/β-gal yield by 3-7 fold compared to wild-type Ad5 infection alone (FIG. 4, lane 2). These data demonstrated that Rep52/40 supplementation can dramatically increase infectious rAAV-2 yields from stable cell lines such as HeLa cell lines (or transformed 293 cell lines).

EXAMPLE 5

Stable rAAV Producer Cells Lines with an Additional rep52/40 Gene Expression Cassette The rep52/40 proteins may be overexpressed in a stable cell line to achieve enhanced yields of rAAV.

A series of HeLa rAAV producer cell lines that harbored an additional rep-52/40gene expression cassette .was generated. To allow for adenovirus inducible expression, the tet-responsive element promoter (TRE) was employed to, drive Rep52/40 expression. Accordingly, the TRE-rep52/40 cassette was cloned into the rAAV/β-gal producer plasmid and generated plasmid pAAV/CMV/β-gal/rep-cap/TRE-rep52/40/neotk. Producer cell lines were isolated as described above. Western blot analysis revealed that the 2F10β, 2B9, and 2G2 cell lines all expressed higher levels of the rep52/40 proteins after Ad5 infection compared to standard HeLa producer cell lines (like line D6). Moreover, enhancement in single-strand vector DNA accumulation was also observed in these lines compared to the standard D6 cell lines, which is consistent with enhanced small rep protein synthesis in these modified cell lines.

Figure 5:
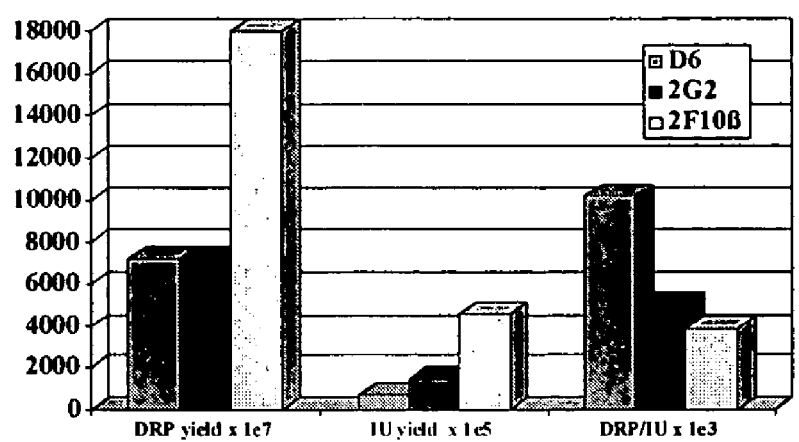
FIG. 5 shows overexpression of Rep52/40 in cell lines 2F10β and 2G2 augments rAAV yields.

In addition, a direct rAAV/β-gal yield comparison between the standard D6line and two Rep52/40 overexpressing cell lines (2G2 and 2F10β) was performed. A total of 3×10$^7$ cells were Ad5 infected (moi=20) and 48 hr later a clarified cell lysate was obtained. DNA containing particles (DRP) were quantified using real-time Taqman PCR (CMV primer/probe) for each cell line. Infectious rAAV/β-gal particles in the lysates were measured by diluting the lysate 1,000-fold and infecting an indicator cell line (C12+Ad5) for 24 hr. β-gal positive cells per well (2 wells total) were counted following X-gal staining the data shown is the average of the 2 well total. Results are shown in FIG. 5.

Both rep52/40 modified cell lines outperformed the rAAV2/β-gal producer cell line (D6), in terms of total particles (DRP) and infectious vector yields (IU) by 2-6.5 fold. These data strongly suggest that rep52/40 overexpression in a stable cell line context is an effective method to augment rAAV yields.

EXAMPLE 6 rAAV Production in Cells other than HeLa Cells

The rAd5/E3/TRE-rep52/40 may also be used in rAAV production systems involving cells that are not transformed cancer cells such as low passage 293 cells (human embryonic kidney cells transformed with Ad E1), MRC-5 cells (human fetal fibroblasts), WI-38 cells (human fetal fibroblasts), Vero cells (monkey kidney cells) and FRhL-2 cells (rhesus fetal lung cells). Vero and MRC-5 cells have been used to produce numerous human vaccines, including poliovirus (both oral and inactivated) and rabies vaccines. The safety of the cell lines has been demonstrated by pharmacovigilance of >100 million doses of inactivated poliovirus vaccine, >20million doses of rabies vaccine, and >100 billion doses of oral (live) polio vaccine.

Vero cell lines containing all the genetic elements required to produce rAAV were generated. Low passage Vero cells (ATCC CCL-81) were transfected with a tripartite plasmid containing a rAAV genome encoding green fluorescent protein, AAV rep and cap genes and the neo gene as described in Clark et al., *Hum. Gene Ther.*, 6: 1329-1341 (1995). Following G418 drug selection and cell line screening, 4 of 70 clones (C2, D1, C24 and E11) were found to produce rAAV2/eGFP viral particles when infected with Ad5. Two of the cell lines (C2 and D1) were compared in a small-scale production run to a HeLa line (2F10) which also produces the rAAV2/eGFP particles. The yield of infectious rAAV2/eGFP from the Vero-derived C2 line was 61-fold lower than virus particles produced by the 2F10 HeLa cell line.

TABLE 1

Production of rAAV2/eGFP From Vero Producer Cell Lines.

| Cell Line[1] | DRP Yield[2] | GFU Yield[3] | DRP/GFU |
|---|---|---|---|
| C2 (Vero) | 7.7e8 | 2.3e7 | 33 |
| D1 (Vero) | 1.1e8 | 8.5e6 | 13 |
| 2F10 (HeLa) | 4e10 | 1.4e9 | 29 |

[1]Ad5 moi was 20.
[2]DRP yield from 10$^7$ cells; eGFP specific Taqman PCR primer/probe set.
[3]eGFP infectious fluorescent units; counted on a rep expressing HeLa cell line (C12) + Ad To investigate the difference in rAAV yields between the Vero and HeLa producer cell lines, capsid levels and rep-cap gene amplification were analyzed.

For AAV2 capsid detection, 2F10 HeLa, C2 Vero and D1 Vero producer cell line membranes were incubated with a 1:10 dilution of an anti-cap mouse monoclonal antibody (Clone B1, American Research Products, Inc.) Following three PBS washes, the membrane was incubated with either an anti-mouse IgG antibody conjugated with horseradish peroxidase (1:10,000 dilution). Protein visualization was achieved using an enhance chemiluminescence peroxidase substrate (ECL, Amersham Life. Sciences).

To analyze rep-cap gene amplification in producer cell lines, Southern blot analysis was performed on 10 μg total cellular DNA from the 2F10 HeLa cells and C2 Vero cells. 48 hours after Ad5 infection, DNA was digested with SpeI (cuts once in the plasmid) and hybridized with a 4.3 kb rep-cap gene DNA fragment.

Capsid levels were significantly lower in both Vero cell lines compared to the HeLa cell line. This contributed to lower particles yields in the Vero lines because capsid levels must reach a minimal intranuclear concentration before particle formation occurs. Moreover, the level of rep-cap gene amplification was also attenuated. 2F10 HeLa cells amplified the rep gene >100-fold after Ad5 infection, while Ad5 induced only a 3-fold rep gene amplification in C2 Vero cells.

These experiments indicated that Ad5 helper functions could be improved, for example, by use of the rAd5/E3/TRE-rep52/40 described herein. In addition, one group I simian adenovirus (SV-20), when substituted for the human Ad5 helper virus in the Vero cell production system described above, was found to increase rAAV/eGFP yield 24-fold. C2 Vero and 2F10 HeLa rAAV2/eGFP producer cells were infected over a range of moi (1, 10, 100) with Ad5 or one of four simian Ad [SV-15 (ATCC VR-1449), SV-20 (ATCC VR-199), SV-27 (ATCC VR-202) or SV-32(VR-205)]. Forty-eight hours after infection, cells were collected, heat inactivated at 56° C. and subjected to 3 freeze/thaw cycles to release rAAV/eGFP. Clarified lysate dilutions were prepared and used to infect C12 cells (AAV2 Rep expressing cell line) and green fluorescent cells (GFU) were counted at 36 hours post-infection. Results are presented in FIG. 6. Analysis of AAV2 rep gene amplification in the C12 cells infected (data not shown) was consistent with the increased yield observed, showing 10-fold rep gene amplification with Ad5 infection, 65-fold amplification with SV-15 infection or 145-fold amplification with SV-20 infection.

In other rAAV production systems, cells that are to produce rAAV may be infected with E3-deleted rAd encoding Rep52/40 proteins, E3-deleted rAd encoding AAV cap proteins and E3-deleted rAd containing a gene of interest (or a gene expresstion cassette wherein the gene of interest is operatively linked to a promoter and polyadenylation signal if the gene is to be expressed) flanked by AAV ITRs and are also infected with vaccinia virus encoding AAV Rep78/68 proteins. This approach can be particularly useful for cells (such as MRC-5 or WI-38 cells) that undergo senescence after a limited number of population doublings. The approach is referred to as the quad-infection (QI) approach below. Leonard and Berns, *Virology*, 200: 566-573 (1994) describes methods that can be used to generate vaccinia virus for the system.

One such vaccinia virus was generated by homologous recombination between wild-type vaccinia (WR strain) and the pSC65 recombinant vaccinia cloning vector containing the AAV2 Rep78 coding sequence. Several recombinant Rep78 vaccinia viruses (rVV/Rep78) were isolated and plaque purified and demonstrated to express Rep78 protein.

Figure 6:
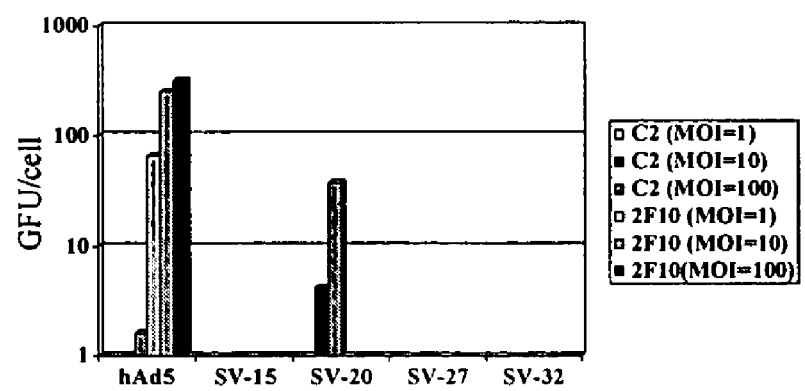
FIG. 6 shows the results of an experiment evaluating simian adenoviruses as helper viruses for rAAV production.

The rVV/Rep78 was used to produce rAAV2/eGFP in HeLa cells by QI. With reference to FIG. 6, HeLa cells were infected with: Lanes 1 and 2, rAAV2/eGFP alone (moi=500); Lane3 (-cap), rAAV2/eGFP (moi=500)+rVV/ATGRep78 (moi=0.5 IU), rAd/E3/Rep52/40 (moi=3 IU); Lane4 (-cap), rAAV2/eGFP (moi=500)+rVV/ACGRep78(moi=0.5 IU), rAd/E3/Rep52/40 (moi=3 IU); Lane5 (−ATGRep78), rAAV2/eGFP (moi=500)+rAd/E3/Rep52/40 (moi=3 IU)+ Ad/E1/Cap (moi=5 IU)+wt VV (moi=0.5 IU); Lane 6 (-ACGRep78), rAAV2/eGFP (moi=500)+,rAd/E3/Rep52/40 (moi=3 IU)+rAd/E1/Cap (moi=5 IU) +wt VV (moi=0.5 IU); lane7 (+positive control), rAAV2/eGFP (moi=500)+plasmid pBS/rep-cap+Ad5; Lane8 (-Rep52/40), rAAV2/eGFP (moi=500)+rAd/E1/Cap (moi=5 IU)+rVV/ATGRep78 (moi=0.5 IU); Lane 9 (QI), rAAV2/eGFP (moi=500)+rVV/ATGRep78 (moi=0.5 IU), rAd/E3/Rep52/40 (moi=3 IU) +rAd/E3/Rep52/40 (moi=3 IU); Lane 10 (QI), rAAV2/eGFP (moi=500)+rVV/ACGRep78(moi=0.5 IU), rAd/E3/Rep52/46 (moi=3 IU)+rAd/E3/Rep52/40(moi=3 IU). After 48, hours, infected HeLa cells were harvested and a clarified cell lysate was generated. To measure infectious rAAV/eGFP production, the lysate was diluted 1,000-fold and used to infect an indicator cell line (C12+Ad5); eGFP positive cells per well (2 wells) were counted after 24 hours and the data shown is the average of the 2 well total.

Figure 7:
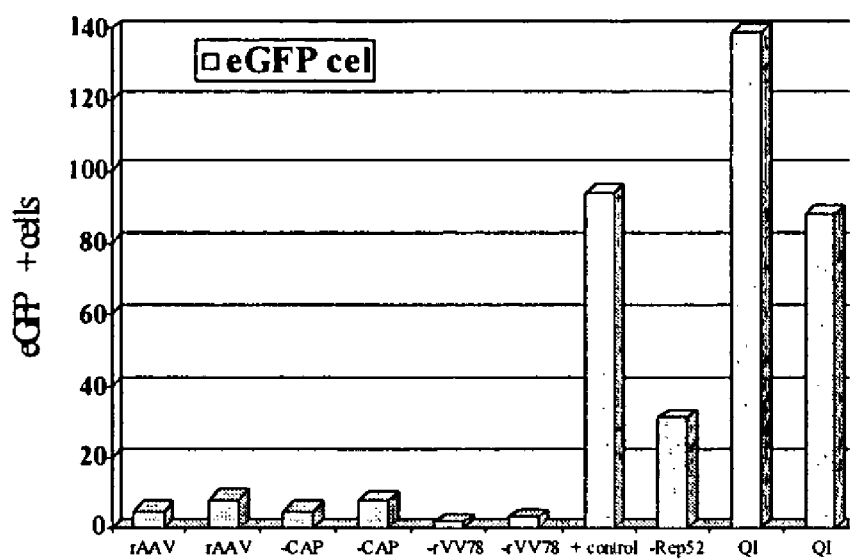
FIG. 7 shows production of infectious rAAV following quad-infection of HeLa cells.
Figure 8:
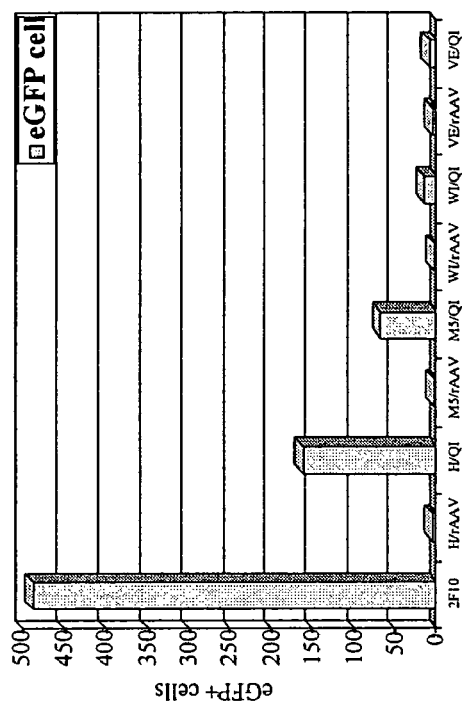
FIG. 8 shows production of infectious rAAV following quad-infection of MRC-5 cells.

When all four viruses (rAAV vector, rAd/Cap, rAd/Rep52/40, rVV/Rep78) were present (lanes 9 and 10) significant levels of rAAV were synthesized (in excess of the positive control; lane 6). The effect of omission of the Rep52/40 proteins can be seen in lane 8 where there was a 3-5 fold reduction in infectious rAAV/eGFP yield. These data demonstrate that the QI approach is indeed a viable option for rAAV production.

rAAV were then produced by the QI approach in several non-transformed cell lines (MRC-5, Vero, and WI-38). With reference to FIG. 7, the indicated cell lines HeLa (H), MRC-5 (M5), WI-38 (WI), and Vero (VE) were infected by either rAAV2/eGFP (moi=500) alone (lanes 2,4,6,8) or QI (lanes 3,5,7,9) using rAAV2/eGFP (moi=500)+rVV/ATGRep78 (moi=0.5 IU), rAd/E3/Rep52/40 (moi=3 IU) +rAd/E3/Rep52/40 (moi=3 IU). As a positive control, an optimal HeLa rAAV/eGFP producer cell line (2F10) was infected with Ad5 alone to initiate high-level rAAV/eGFP production (lane 1). After 48 hr, infected cells were harvested and a clarified cell lysate was generated. To measure infectious rAAV/eGFP production, the lysate was diluted 1,000-fold and used to infect an indicator cell line (C12+Ad5); eGFP positive cells per well (2 wells total) were counted after 24 h and the data shown is the average of the 2 well total.

Using the QI approach, MRC-5 cells yielded only 2-fold less rAAV than the control HeLa producer cell line (lane 1).

In yet another alternative system, the cells are infected with E3-deleted rAd both encoding AAV cap proteins and containing an ITR flanked gene of interest (or gene expression cassette) and infected with vaccinia virus encoding both the AAV Rep78/68 and Rep52/40 proteins.

EXAMPLE 7

Purification of rAAV rAAV may be purified from producer cells as follows or by other methods standard in the art. Following development of Ad 5 cytopathic effect (CPE), the cells are collected and a clarified lysate generated. Residual Ad 5 or vaccinia is inactivated by brief heat treatment and rAAV vector is isolated by heparin affinity column purification (for rAAV-2 vectors) or by iodixanol/anionic exchange column purification (for rAAV-1 or rAAV-5 vectors). Upon final elution, the stock is dialyzed with PBS (pH 7.4), then sterile filtered and supplemented with 5% glycerol.

While the present invention has been described in terms of various embodiments and examples, it is understood that variations and improvements will occur to those skilled in the art. Therefore, only such limitations as appear in the claims should be placed on the invention.

We claim:

1. A recombinant adeno-associated virus (rAAV)-producing cell,
wherein said rAAV-producing cell comprises a rAAV genome, AAV rep-cap proteins and AAV helper functions,
wherein said rAAV-producing cell expresses AAV Rep 78 and Rep 68 proteins at the level of expression of the proteins when under the control of the AAV p5 promoter and the level of expression of AAV Rep 78 and Rep 68 proteins has not been genetically down-regulated,
and wherein said rAAV-producing cell has been modified with an additional expression cassette encoding AAV Rep 52 and Rep 40 proteins but not AAV Rep 78 and Rep 68 proteins.

2. A method of producing infectious rAAV comprising the step of culturing a rAAV-producing cell according to claim 1.

3. A method of generating a rAAV-producing cell, comprising the steps of:
a) providing AAV helper functions to a cell comprising a rAAV genome and AAV rep-cap proteins by infecting said cell with helper virus of AAV or by expressing helper virus proteins in said cell, and
b) then subsequently introducing into the cell an additional expression cassette encoding AAV Rep 52 and Rep 40 proteins but not AAV Rep 78 and Rep 68 proteins.

4. The method of claim 3 wherein the expression cassette in step b) is in a recombinant adenovirus (rAd).

5. The method of claim 4 wherein the rAd is a E3-deleted rAd.

6. The method of claim 4 wherein the rAd is a E1-deleted rAd.

7. The method of claim 4 wherein the rAd is derived from simian Ad SV-20 and retains the ability of Ad SV-20 to introduce the expression cassette encoding AAV Rep 52 and Rep 40 proteins into said cell.

8. A method of generating a rAAV-producing cell, comprising the steps of:
a) introducing an additional expression cassette encoding supplemental AAV Rep 52 and Rep 40 proteins but not AAV Rep 78 and Rep 68 proteins into a cell comprising a rAAV genome and AAV rep-cap proteins, and
b) providing AAV helper functions to the cell by infecting said cell with helper virus of AAV or by expressing helper virus proteins in said cell.

9. The method of claim 8 wherein AAV helper functions of step b) are provided by a helper virus of AAV.

10. The method of claim 9 wherein the helper virus of AAV virus is adenovirus (Ad).

11. The method of claim 10 wherein the adenovirus is simian Ad SV-20.

12. A method of generating a rAAV-producing simian cell comprising the step of:
a) infecting with a simian Ad, a simian cell stably transformed with a rAAV genome and rAAV rep-cap DNA and modified with an additional expression cassette encoding AAV Rep 52 and Rep 40 proteins but not AAV Rep 78 and Rep 68 proteins.

13. The method of claim 12 wherein the simian Ad is SV-20.

14. A method of producing infectious rAAV comprising the step of culturing a rAAV-producing cell generated by the method of claim 3, 8 or 12.

15. The method of any of claims 2, 3 or 8, wherein said rAAV-producing cells are HeLa cells.

16. The method of any of claims 2, 3 or 8 wherein said rAAV-producing cells are 293 cells.

17. The method of any of claims 2, 3 or 8, wherein said rAAV-producing cells are low passage 293 cells.

18. The method of any of claims 2, 3 or 8 wherein said rAAV-producing cells are PerC.6 cells.

19. The method of any of claims 2, 3, 8 or 12, wherein said rAAV-producing cells are Vero cells.

20. The method of any of claims 2, 3, 8 or 12 wherein said rAAV-producing cells are FRhL-2 cells.

21. The method of any of claims 2, 3 or 8 wherein said rAAV-producing cells are MRC-5 cells.

22. The method of any of claims 2, 3 or 8, wherein said rAAV-producing cells are WI-38 cells.

23. The cell of claim 1 that is a HeLa, 293, low passage 293, PerC.6, Vero, FRhL-2, MRC-5 or WI-38 cell.

24. The method of claim 14 wherein said rAAV-producing cells are HeLa cells.

25. The method of claim 14 wherein said rAAV-producing cells are 293 cells.

26. The method of claim 14 wherein said rAAV-producing cells are low passage 293 cells.

27. The method of claim 14 wherein said rAAV-producing cells are PerC.6 cells.

28. The method of claim 14 wherein said rAAV-producing cells are Vero cells.

29. The method of claim 14 wherein said rAAV-producing cells are FRhL-2 cells.

30. The method of claim 14 wherein said rAAV-producing cells are MRC-5 cells.

31. The method of claim 14 wherein said rAAV-producing cells are WI-38 cells.

* * * * *

SEQUENCE LISTING

```
<160> NUMBER OF SEQ ID NOS: 3

<210> SEQ ID NO 1
<211> LENGTH: 2061
<212> TYPE: DNA
<213> ORGANISM: Artificial sequence
```

<220> FEATURE:
<223> OTHER INFORMATION: Restriction fragment of plasmid pTRE-Rep52/40

<400> SEQUENCE: 1

```
attattgaag catttatcag ggttattgtc tcatgagcgg atacatattt gaatgtattt      60
agaaaaataa acaaataggg gttccgcgca catttccccg aaaagtgcca cctgacgtct     120
aagaaaccat tattatcatg acattaacct ataaaaatag gcgtatcacg aggccctttc     180
gtcctcgagt ttaccactcc ctatcagtga tagagaaaag tgaaagtcga gtttaccact     240
ccctatcagt gatagagaaa agtgaaagtc gagtttacca ctccctatca gtgatagaga     300
aaagtgaaag tcgagtttac cactccctat cagtgataga gaaaagtgaa agtcgagttt     360
accactccct atcagtgata gagaaaagtg aaagtcgagt ttaccactcc ctatcagtga     420
tagagaaaag tgaaagtcga gtttaccact ccctatcagt gatagagaaa agtgaaagtc     480
gagctcggta cccggggtcga gtaggcgtgt acggtgggag gcctatataa gcagagctcg     540
tttagtgaac cgtcagatcg cctggagacg ccatccacgc tgttttgacc tccatagaag     600
acaccgggac cgatccagcc tccgcggccc cgaattaatt cccaccatgg agctggtcgg     660
gtggctcgtg acaaggggga ttacctcgga gaagcagtgg atccaggagg accaggcctc     720
atacatctcc ttcaatgcgg cctccaactc gcggtcccaa atcaaggctg ccttggacaa     780
tgcgggaaag attatgagcc tgactaaaac cgccccccgac tacctggtgg ccagcagcc     840
cgtggaggac atttccagca atcggattta taaaattttg gaactaaacg ggtacgatcc     900
ccaatatgcg gcttccgtct ttctgggatg ggccacgaaa aagttcggca agaggaacac     960
catctggctg tttgggcctg caactaccgg gaagaccaac atcgcggagg ccatagccca    1020
cactgtgccc ttctacgggt gcgtaaactg gaccaatgag aactttccct caacgactg     1080
tgtcgacaag atggtgatct ggtgggagga ggggaagatg accgccaagg tcgtggagtc    1140
ggccaaagcc attctcggag gaagcaaggt gcgcgtggca cagaaatgca gtcctcggc     1200
ccagatagac ccgactcccg tgatcgtcac ctccaacacc aacatgtgcg ccgtgattga    1260
cgggaactca acgaccttcg aacaccagca gccgttgcaa gaccggatgt tcaaatttga    1320
actcacccgc cgtctggatc atgacttgg gaaggtcacc aagcaggaag tcaaagactt    1380
tttccggtgg gcaaaggatc acgtggttga ggtggagcat gaattctacg tcaaaaaggg    1440
tggagccaag aaaagacccg cccccagtga cgcagatata agtgagccca acgggtgcg     1500
cgagtcagtt gcgcagccat cgacgtcaga gcggaagct tcgatcaact acgcagacag    1560
gtaccaaaac aaatgttctc gtcacgtggg catgaatctg atgctgtttc cctgcagaca    1620
atgcgagaga atgaatcaga attcaaatat ctgcttcact cacgacaga aagactgtttt    1680
agagtgctttt cccgtgtcag aatctcaacc cgtttctgtc gtcaaaaagg cgtatcagaa    1740
actgtgctac attcatcata tcatgggaaa ggtgccagac gcttgcactg cctgcgatct    1800
ggtcaatgtg gattttggatg actgcatctt tgaacaataa atgatttaaa tcaggtatgg    1860
ctgccgatgg ttatcttcca gattggctcg aggacactct ctctgatcta gctagaggat    1920
ccagacatga taagatacat tgatgagttt ggacaaacca caactagaat gcagtgaaaa    1980
aaatgcttta tttgtgaaat ttgtgatgct attgctttat ttgtaaccat tataagctgc    2040
aataaacaag ttaacaacaa c                                              2061
```

<210> SEQ ID NO 2
<211> LENGTH: 37
<212> TYPE: DNA

-continued

```
<213> ORGANISM: Artificial sequence
<220> FEATURE:
<223> OTHER INFORMATION: Synthetic primer

<400> SEQUENCE: 2
ccgtgaattc ccaccatgga gctggtcggg tggctcg                              37

<210> SEQ ID NO 3
<211> LENGTH: 32
<212> TYPE: DNA
<213> ORGANISM: Artificial sequence
<220> FEATURE:
<223> OTHER INFORMATION: Synthetic primer

<400> SEQUENCE: 3
ccgtgtctag atcagagaga gtgtcctcga gc                                    32
```